United States Patent [19]

Holmes et al.

[11] Patent Number: 4,931,042
[45] Date of Patent: Jun. 5, 1990

[54] TROCAR ASSEMBLY WITH IMPROVED LATCH

[75] Inventors: William A. Holmes, Marblehead; Peter F. Costa, Cambridge, both of Mass.

[73] Assignee: EndoTherapeutics, Menlo Park, Calif.

[21] Appl. No.: 113,013

[22] Filed: Oct. 26, 1987

[51] Int. Cl.$^5$ .............................................. A61M 5/18
[52] U.S. Cl. ................................... 604/164; 606/185
[58] Field of Search ............... 604/117, 164, 165, 157, 604/158, 136, 169, 264, 272, 273, 274; 128/314, 315, 305, 329 R; 403/330, 329, 325; 606/184, 185, 191; 30/151, 152, 366–368

[56] References Cited

U.S. PATENT DOCUMENTS 4,654,030  3/1987  Moll et al. ............................ 604/165

Primary Examiner—Michael H. Thaler
Assistant Examiner—William Lewis
Attorney, Agent, or Firm—Irell & Manella

[57] ABSTRACT

A trocar assembly comprising an elongate trocar obturator having a piercing tip at its front end, an elongate trocar tube in which the obturator is housed, and a tubular protective shield mounted concentrically around the obturator between a normally extended position in which the obturator tip is covered and a retracted position in which the obturator tip is exposed. Further included is a spring acting on the protective shield, whereby the shield is forced to the retracted position to expose the piercing tip when the trocar is being inserted through the wall of a body cavity and is biased by the spring to the extended position to shield the piercing tip once the trocar has pierced the wall. A protrusion extends radially from the shield. A leaf spring element has one end anchored relative to the obturator and a second end biased to contact the protrusion in a manner preventing movement of the shield from the extended position toward the retracted position when the element is in contact with the protrusion. A trigger, coupled to the leaf spring member is shiftable between a lock position and a release position. When the trigger is in the lock position, the shield can not be moved from the extended position. When it is in the release position, the shield can travel to the retracted position. When it moves to the retracted position, it disengages the trigger so that when the shield returns to the extended position, it locks in place, even through the trigger is in the release position.

9 Claims, 3 Drawing Sheets

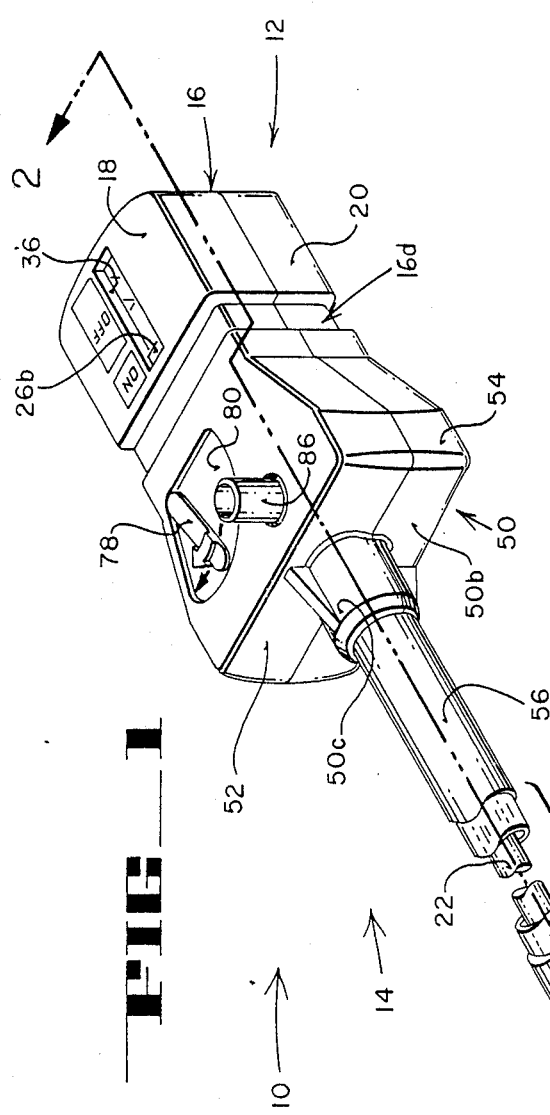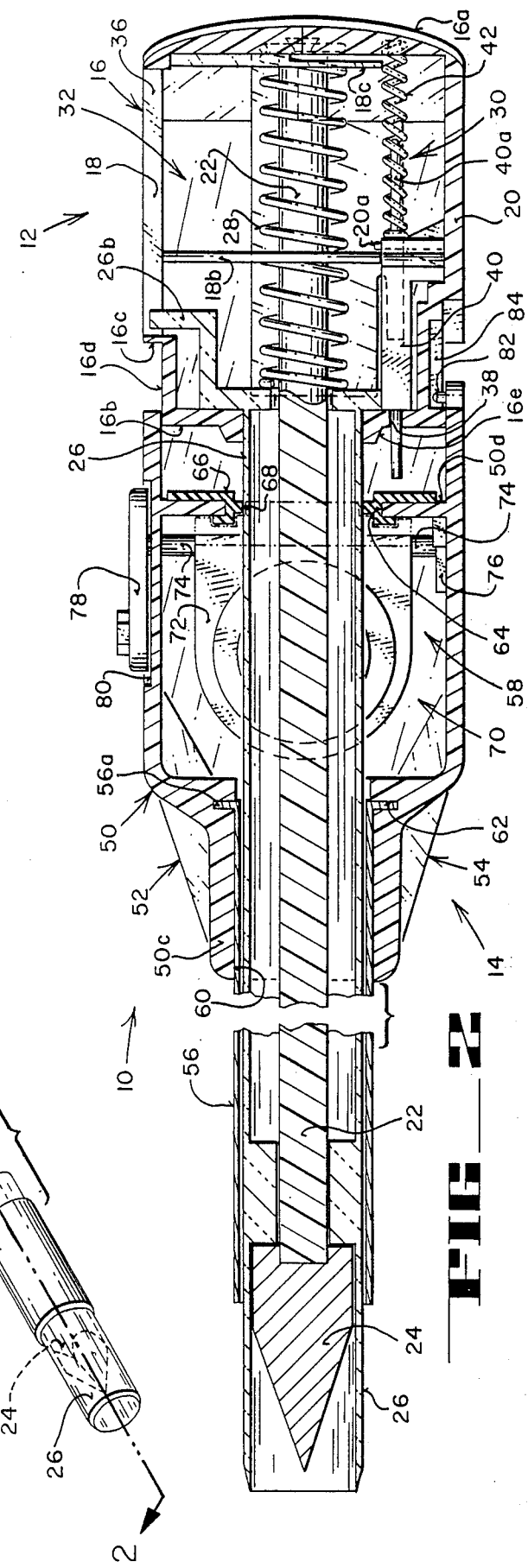

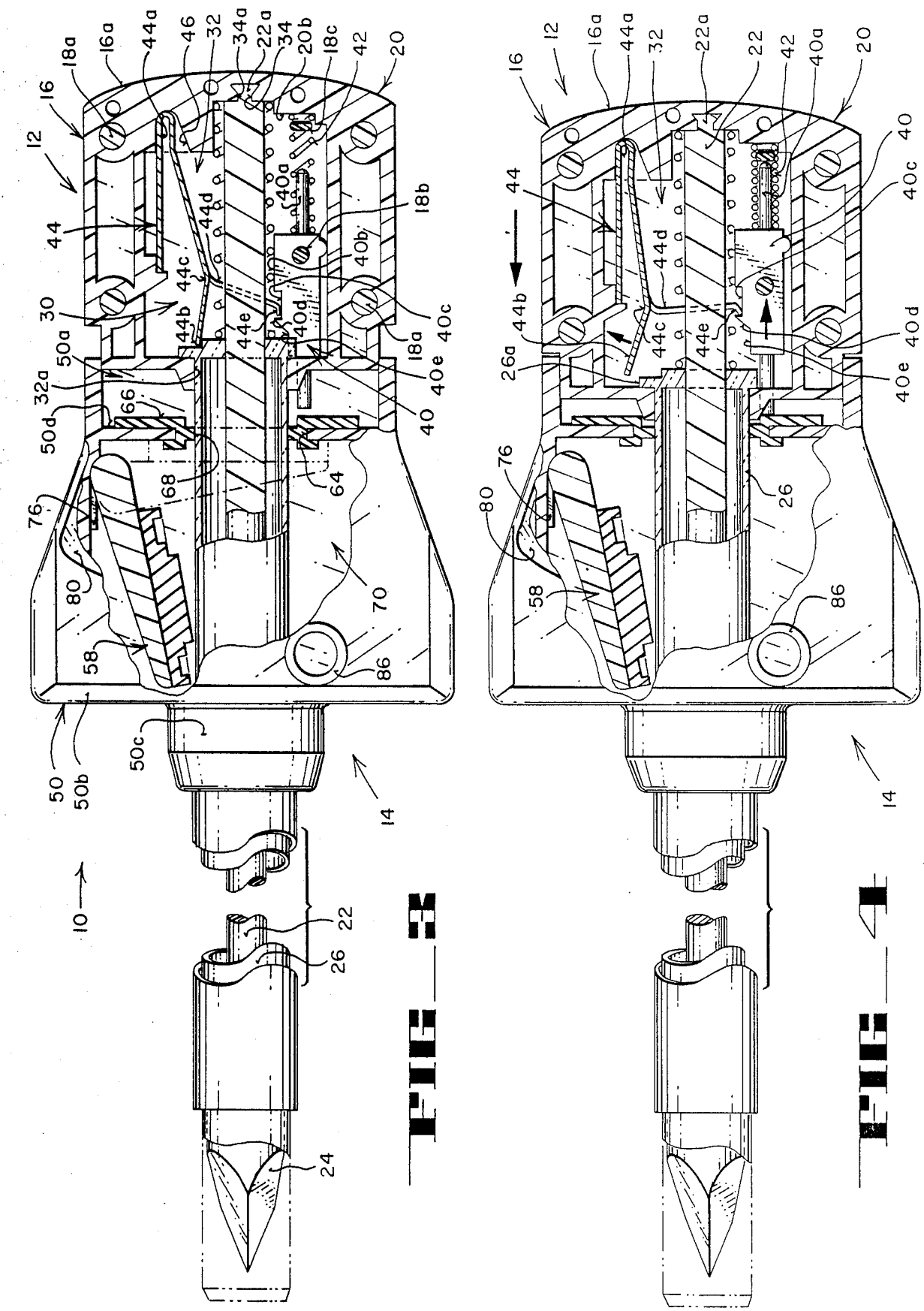

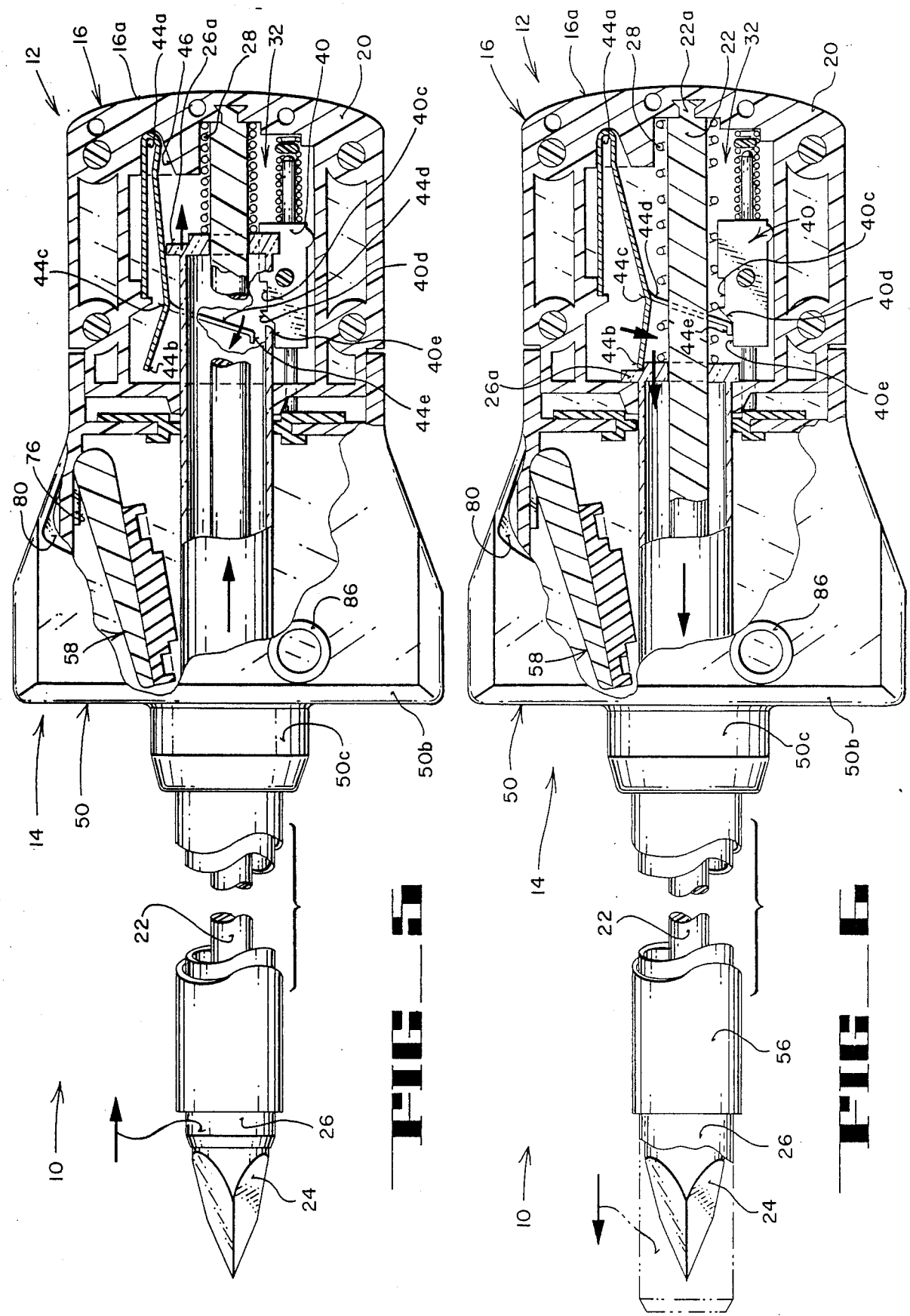

– 4,931,042 –

TROCAR ASSEMBLY WITH IMPROVED LATCH

FIELD OF THE INVENTION

This invention relates to surgical instruments. More particularly, it relates to a trocar assembly with an improved protective shield latch.

BACKGROUND OF THE INVENTION

Trocars are sharp-pointed instruments used to puncture a body cavity. This is often done so that fluids may be drained using a cannula inserted into the opening. Trocars are also used during endoscopic procedures. A conventional endoscopic procedure follows three steps. The first step is the insertion of a Veress cannula into an abdominal cavity through a small incision in the abdominal wall. The cavity is inflated with insufflating gas passed through the cannula. After inflation, the Veress cannula is removed. Finally, a standard trocar housed within the bore of a trocar tube is thrust into the inflated abdomen. Standard trocars are shaped like a large metal peg with a sharpened point. The trocar is then removed and the endoscopic instrument is inserted into the abdominal cavity through the trocar tube.

Commonly owned U.S. Patents having U.S. Pat. Nos. 4,601,710 and 4,654,030 describe three embodiments of a trocar assembly having a spring-biased tubular protective shield. One of the embodiments in the former patent has a shield locking mechanism that comprises a slide valve-actuated locking tooth that engages a slot in the wall of the shield. This mechanism is cumbersome. The latter patent discloses an embodiment wherein the flap valve functions as a shield locking means by having a tip which seats against a recessed shoulder on the shield. The valve is manually controlled to release the shield. This embodiment is also cumbersome in that it requires separate manual manipulation. It was therefore desirable to provide an improved valve which operated simply by the manipulation of relative trocar assembly housings during use of the trocar in a surgical procedure.

SUMMARY OF THE INVENTION

The present invention provides a trocar assembly that is improved over the above-described trocars with respect to the operation of a protective shield latching mechanism.

Accordingly, one aspect of the invention is a trocar assembly comprising an elongate trocar obturator having a piercing tip at its front end. An elongate trocar tube in which the obturator is housed. A tubular protective shield is mounted concentrically around the obturator between a normally extended position in which the obturator tip is covered and a retracted position in which the obturator tip is exposed. A biasing means acts on the rear end of the protective shield, whereby the shield is forced to the retracted position to expose the piercing tip when the trocar is being inserted through the wall of a body cavity and is biased by the biasing means to the extended position to shield the piercing tip once the trocar has pierced the wall. Means are included for preventing the shield from moving from the extended position toward the retracted position.

A trigger means is coupled to the preventing means and operable between a lock position in which the preventing means is effective, and a release position for defeating the preventing means and allowing the shield to move from the extended position toward the retracted position. Means for defeating the trigger means is provided for reactivating the preventing means when the shield is returned from the retracted position to the extended position while the trigger means is maintained in the release position.

BRIEF DESCRIPTION OF THE DRAWINGS

FIG. 1 is an isometric view of a preferred embodiment of the trocar assembly of the present invention.

FIG. 2 is an enlarged sectional view taken along line 2—2 in FIG. 1.

FIGS. 3-6 are partial cross-sectional views taken from above in FIG. 2 illustrating operation of the latch mechanism of the embodiment of FIG. 1.

DETAILED DESCRIPTION OF THE PREFERRED EMBODIMENT

The drawings illustrate a trocar assembly, generally designated 10, that is basically composed of two parts: a trocar subassembly 12 and a trocar tube subassembly 14. The two subassemblies are interfitting, but designed to be separable from each other. The basic elements of trocar subassembly 12 are a hollow housing forming a grip or head 16 composed of nesting halves 18 and 20; an obturator 22 having a piercing tip 24; a generally tubular obturator sleeve or shield 26; a spring 28 for biasing the shield; and a latching mechanism shown generally at 30.

Head 16 has a rounded rear wall 16a that fits comfortably into the palm of the hand and a generally rectangular front wall 16b. Wall 16b has a shoulder 16c that defines a forward raised section shown generally at 16d. The two halves 18 and 20 are generally symmetrical and snap fit together with four posts 18a extending transversely from the inner wall of half 18. The head has a central axial chamber 32 for receiving the obturator and shield. Chamber 32 terminates in a generally triangular-shaped recess 34 (as viewed in FIG. 3) having a narrow neck 34a formed in the inner face of the rear wall into which a matingly formed rear end 22a of the obturator shaft fits to hold the obturator in head 16.

The front wall 16b has a circular opening 32a that is defined by a collar 16e and which opens into chamber 32. As shown in FIGS. 2-6, spring 28 encircles the rear end of the obturator shaft with its ends seated against the inner face of the rear wall of the grip and the rear end wall of the shield. The side face of head half 18 has an axially elongate opening 36. Formed as part of the rear end of shield 26 is a protrusion or lip 26a which extends radially from the shield in line with the joint between head halves 18 and 20. Extending upwardly and rearwardly from the rear end of the shield is a position-indicating finger 26b which extends into opening 36 for indicating the position of the shield relative to the obturator.

Disposed in head half 20, generally opposite from the position of lip 26a is a bore 38. Extending through, this bore for sliding movement relative to head 16 along an axis parallel with the longitudinal axis of the shield and obturator is a trigger 40. Trigger 40 extends through raised section 16d with an exposed forward extending tip. The end of the trigger in chamber 32 is biased toward bore 38 by a spring 42 which extends between the end of the trigger and the rear wall of head 16 in head half 20. A rod section 40a is formed in the end of the trigger and extends toward the rear wall of chamber 32 and is sized to be received in spring 42 for aiding in holding the spring in alignment against the end of the trigger. The trigger is further maintained in alignment relative to the chamber by a guide 20a positioned next to the side of the trigger and another guide 18b extending from the face of head half 18 adjacent opening 36 to the corresponding surface of the trigger. The end of spring 42 disposed against the rear inner wall of head half 20 is held in position by a partial channel 20b in which it is seated and an arm 18c extending from head half 18 and seating against the spring end seated against the inner wall.

The side of the trigger adjacent to guide 20a has three generally planar sections. A guide section 40b is disposed parallel with and adjacent guide 20a. An intermediate section 40c is slightly recessed from section 40b, except for a ridge 40d disposed at the end of section 40c adjacent to the exposed tip of the trigger. Finally, a further recessed end section 40e is also adjacent to the forward side of ridge 40d.

Opposite from trigger 40 in the portion of chamber 32 defined by head half 20 is a leaf spring member 44. As viewed in FIGS. 3–6, Member 44 has a general narrow V-shape with the base 44a of the "V" seated in a correspondingly V-shaped cavity 46 in head half 20. One leg of the spring member is pressed against the side of chamber 32. The end 44b of the other leg is free standing and disposed adjacent collar 16e where it seats in a block position against lip 26a of the shield when the trigger is positioned in what is referred to as a lock position with the exposed trigger tip extended. The leaf spring member thus is also referred to as a second biasing means for biasing end 44b in the block position. End 44b is accordingly also referred to as a stop or means for preventing the shield from moving to the extended position. Leaf spring member 44 has a bend 44c in it intermediate the V-base and end 44b. This bend puts the intermediate portion of the leaf spring member closer to trigger 40. A portion or arm 44d, also referred to as link means, of member 44 extends toward trigger 40. The distal end or tip 44e of arm 44d has a slight curve, with the curved portion seated on trigger side portion 40c and against ridge 40d with the trigger in the lock position and the shield in the extended position as shown in FIG. 3.

The basic elements of trocar tube subassembly 14 are: a main body 50 composed of two generally symmetrical halves 52 and 54 that are held together by appropriate fastening means; an axially elongate trocar tube 56; and a flap valve mechanism 58. The rear end of body 50 has a rectangular recess 50a that mates with raised section 16d on the front end of the grip of the trocar subassembly when the two subassemblies are interfitted.

A front wall 50b of the body is curved to facilitate gripping the trocar with the fingers and has a circular opening 60 defined by a collar 50c in which the trocar tube is mounted. The rear end of opening 60 expands into a circumferential groove 62 into which a collar 56a on the rear end of the trocar tube is seated to fix the tube within collar 50c.

A rear wall 50d of the body has a central circular opening 64 in which a rubber grommet 66 is seated. Grommet 66 has a central opening 68 coextensive with opening 64. The obturator and shield are sized to pass through the central grommet opening with the grommet forming a seal around the shield.

Body 50 has an inner cavity 70 into which openings 60 and 64 open and in which flap valve mechanism 58 is mounted. The flap valve mechanism includes a U-shaped flapper 72, a shaft 74 which traverses the cavity and on which the flapper is carried, a spring 76 disposed about one end of the shaft, and an actuating lever/indicator 78 carried on one end of the shaft exteriorly of the body. The exterior of the body at the location of the indicator has a fan shaped recess 80 in which the indicator moves.

When the obturator and sleeve are inserted in opening 68, the flapper valve opens, allowing the obturator and sleeve to be fully inserted in trocar tube 56. The indicator thus swings from a position indicating that opening 68 is sealed to a position indicating it is open. A lower lip lining an edge of the recessed rear wall 50d has a nipple 82 extending inwardly. The lower, outwardly facing edge adjacent raised portion 16d corresponding in position to the nipple has a slot 84 in which the nipple travels during normal use of the trocar assembly with the two subassemblies joined. When the obturator subassembly is removed from the trocar tube assembly, the nipple is removed from the slot to allow separation.

The trocar assembly operates and is used as follows. Prior to use, the trocar assembly will typically be in the assembled form shown in FIGS. 1–3 with the raised rectangular section 16d fitting into recess 50a, and with the obturator and shield inserted through the opening in grommet 66, cavity 70, and the lumen of trocar tube 56.

The trocar shield is normally locked in its extended position as shown in FIGS. 1–3 for safety purposes and for storage. In this position the piercing tip is shielded and cannot be damaged by inadvertent contact with other surfaces. In this locked position spring 28 biases shield 26 forwardly with lip 26a limiting the forward travel by contact against the inner surface of front wall 16b. The bias of leaf spring member 44 keeps end 44b seated against lip 26a, preventing rearward movement of the shield.

In order to unlock the shield, head 16 is pressed toward main body 50 to the position shown in FIG. 4. By doing so, raised section 16d, with the exposed tip of trigger 40 protruding, is inserted into recess portion 50a. Rear wall 50d is forced against the tip of the trigger, causing the trigger to retract into chamber 32 to what is referred to as a release position. This movement usually takes place when the shield and obturator tip are placed against an incision in the skin and pressure is exerted against the skin by pressing against head 16. Pressure on the head of the trocar assembly concurrently shifts the trigger to the release position while applying force against the skin tissue. The tip enters the incision and underlying tissue with continued pressure.

As the trigger moves to the release position, end 44e of leaf spring member arm 44d is carried with it since ridge 40d prevents the end from sliding along the trigger side. This puts arm 44d in a more perpendicular alignment across chamber 32, forcing free end 44b laterally away from the shield, and therefore away from lip 26a, as shown in FIG. 4. With leaf spring member end 44b displaced from lip 26a, shield 26 is free to move rearwardly, exposing obturator tip 24. The force of the body cavity wall tissue on the shield forces it into the retracted position shown in FIG. 5.

As the shield moves rearwardly, lip 26a contacts the side of leaf spring member 44 between free end 44b and bend 44c. Because of the angle of the leaf spring, it acts like a cam with lip 26a to further displace free end 44b away from shield 26 to what is referred to as a withdrawn position. Concurrently with this, the end 44e of arm 44d is also displaced from side section 40c and ridge 40d. The arm is biased toward the exposed tip of the trigger so that as its end clears the ridge, it snaps into a position adjacent side section 40e. This is the configuration shown in FIG. 5. The devices providing this cam action are therefore also referred to collectively as means for reactivating the blocking function of leaf spring free end 44b.

Once the tip has penetrated the tissue and has entered the cavity, the force against the front end of the shield ceases and the shield is automatically moved axially back to its extended position through the action of spring 28. Even with the two subassemblies pressed together and trigger 40 in its release position, free end 44b of the leaf spring member seats against lip 26a when the shield returns to the extended position. This configuration is shown in FIG. 6. Thus, while the obturator tip remains in the body cavity, its tip is protected by the protective shield which is locked into the protective position so that the tip will not accidentally cut viscera and other internal tissue unintentionally.

The trocar subassembly may be withdrawn from the trocar tube subassembly once the cavity has been penetrated. In this operation, pressure is released from head 16. Spring 42 is strong enough to push the subassemblies apart, thereby returning the trigger to the lock position shown in FIG. 3 with the leaf spring member arm end 44e back in place against trigger side section 40c. The obturator and shield are slid out of trocar tube 56 and main body 50. Spring 76 then forces flapper 72 against grommet 66, sealing opening 68. Air pressure within the body cavity is thus maintained. In this regard, body half 52 of body 50 is equipped with a stopcock port 82 into which the nozzle of a stopcock (not shown) is inserted. The stopcock will normally be closed during the trocar insertion to maintain the gas pressure within the body cavity. If necessary, the stopcock may be used as a conduit for passing additional insufflating gas into the cavity.

After the obturator subassembly has been separated from the trocar tube subassembly, surgical instruments may be inserted into the body cavity via the trocar tube subassembly to view internal tissues, perform operations thereon, or drain body fluids. Indicator 78 may be used as a handle to manually open valve flapper 76 to facilitate such activities and also permit the removal of specimens and to deflate the cavity.

While a preferred embodiment has been used to illustrate the present invention, it will be understood that variations in form and detail may be made without varying from the scope and spirit of the invention as defined in the claims. For example, the function of the trigger, spring leaf member, and shield protrusion could be effected by appropriate sequencing of overlapping cam surfaces. Other equivalent modifications will also be apparent to one skilled in the art of mechanical engineering, surgical instrument design, or related fields.

What I claim is:

1. A trocar assembly comprising:
   an elongate trocar obturator having a piercing tip at its front end;
   an elongate trocar tube in which said obturator is housed;
   a tubular protective shield mounted concentrically around said obturator between a normally extended position in which said obturator tip is covered and a retracted position in which said obturator tip is exposed; and
   biasing means acting on said protective shield, whereby said shield is forced to said retracted position to expose said piercing tip when said trocar is being inserted through the wall of a body cavity and is biased by said biasing means to said extended position to shield said piercing tip once said trocar has pierced the wall;
   means for preventing said shield from moving from said extended position toward said retracted position;
   trigger means coupled to said preventing means and operable between a lock position in which said preventing means is effective, and a release position for defeating said preventing means and allowing said shield to move from said extended position toward said retracted position, said trigger means being automatically actuable upon application of pressure against said tubular protective shield; and
   means for reactivating said preventing means when said shield is returned from said retracted position to said extended position while said trigger means is maintained in said release position.

2. A trocar assembly according to claim 1 wherein said preventing means includes a stop engageable with said shield preventing travel of said shield toward said retracted position, said assembly further comprising second biasing means for urging said stop from a retracted position in which said shield is unhindered in traveling between said extended and retracted positions toward a block position in which said stop engages said shield.

3. A trocar assembly according to claim 1 wherein said reactivating means uncouples said trigger means from said preventing means when said shield is moved from said extended position toward said retracted position.

4. A trocar assembly according to claim 3 further comprising link means coupling said trigger means to said preventing means, said reactivating means including means for separating said link means from one of said trigger means and said preventing means.

5. A trocar assembly comprising:
   an elongate trocar obturator having a piercing tip at its front end;
   an elongate trocar tube in which said obturator is housed;
   a tubular protective shield mounted concentrically around said obturator between a normally extended position in which said obturator tip is covered and a retracted position in which said obturator tip is exposed; and
   biasing means acting on said protective shield, whereby said shield is forced to said retracted position to expose said piercing tip when said trocar is being inserted through the wall of a body cavity and is biased by said biasing means to said extended position to shield said piercing tip once said trocar has pierced the wall;
   means for preventing said shield from moving from said extended position toward said retracted position;
   trigger means coupled to said preventing means and operable between a lock position in which said preventing means is effective, and a release position for defeating said preventing means and allowing said shield to move from said extended position toward said retracted position; and means for reactivating said preventing means when said shield is returned from said retracted position to said extended position while said trigger means is maintained in said release position;

wherein said reactivating means uncouples said trigger means from said preventing means when said shield is moved from said extended position toward said retracted position;

said trocar assembly further comprising link means coupling said trigger means to said preventing means, said reactivating means including means for separating said link means from one of said trigger means and said preventing means; and wherein said link means includes one end pivotably coupled to one of said trigger means and said preventing means, the other end of said link means being movable between a first position in which said other link means end is captured against the other of said trigger means and said preventing means during movement of said trigger from said lock position to said release position, and a second position in which said other link means end allows said preventing means to be reactivated, said defeating means being for moving said other link means end from said first position to said second position.

6. A trocar assembly comprising:

an elongate trocar obturator having a piercing tip at its front end;

an elongate trocar tube in which said obturator is housed;

a tubular protective shield mounted concentrically around said obturator between a normally extended position in which said obturator tip is covered and a retracted position in which said obturator tip is exposed; and biasing means acting on said protective shield, whereby the shield is forced to said retracted position to expose said piercing tip when said trocar is being inserted through the wall of a body cavity and is biased by said biasing means to said extended position to shield said piercing tip once said trocar has pierced the wall;

a trigger shiftable between a lock position and a release position;

a protrusion extending radially from said shield;

a stop shiftable between a block position in which said stop is engaging said protrusion for preventing movement of said shield from said extended position toward said retracted position, and a withdrawn position in which said stop is removed from said protrusion;

means coupling said trigger to said stop in a manner wherein said stop shifts from said block position to said withdrawn position when said trigger is shifted from said lock position to said release position; and cam means for uncoupling said trigger from said member by moving said member beyond said withdrawn position.

7. A trocar assembly according to claim 6 wherein said trigger and stop are coupled in a manner wherein said shield is movable from said retracted position to said extended position and said stop is biased to shift to said block position when said shield is moved to said extended position while said trigger is in said release position.

8. A trocar assembly comprising:

an elongate trocar obturator having a piercing tip at its front end;

an elongate trocar tube in which said obturator is housed;

a tubular protective shield mounted concentrically around said obturator between a normally extended position in which said obturator tip is covered and a retracted position in which said obturator tip is exposed;

biasing means acting on said protective shield, whereby said shield is forced to said retracted position to expose said piercing tip when said trocar is being inserted through the wall of a body cavity and is biased by said biasing means to said extended position to shield said piercing tip once said trocar has pierced the wall;

a protrusion extending radially from said shield;

a leaf spring element having one end anchored relative to said obturator, a second end biased to contact said protrusion in a manner preventing movement of said shield from said extended position toward said retracted position when said element is in a relaxed state, said leave spring element further having a trigger-engaging arm having a distal end and extending from a position intermediate said element ends transverse of the longitudinal axis of said shield;

a trigger shiftable between a lock position and a release position, and including an elongate shaft having a side with a ridge extending transverse of the length of said trigger, said trigger side portion adjacent one side of the base of said ridge being raised relative to the trigger side portion adjacent the other side of said base, said ridge being disposed in a manner wherein said leaf spring element arm distal end seats against said ridge on said raised side portion of said trigger side when said trigger is in said lock position and said leaf spring element second end is seated against said protrusion;

said protrusion, leaf spring element and said trigger being structured in a manner whereby said leaf spring element arm moves said leaf spring element second end away from engagement with said protrusion when said trigger is shifted from said lock position to said release position, said protrusion contacts said leaf spring element intermediate said first and second ends and forces said leaf spring element in a manner removing said arm distal end from the raised side adjacent said trigger ridge, said arm being biased to move said arm distal end adjacent said recessed side of said trigger ridge when removed from said raised side of said trigger ridge, said second end of said leaf spring member returning to said position in contact with said protrusion when said leaf spring arm is adjacent said recessed side of said trigger ridge, and said second end of said leaf spring element engaging said protrusion when said shield moves from said retracted position to said extended position with said trigger remaining in said release position.

9. A trocar assembly according to claim 8 wherein said leaf spring arm adjacent said trigger side moves from said recessed side portion over said ridge to said raised side portion when said shield is in said extended position and said trigger is moved from said release position to said lock position.

* * * * *

Disclaimer

4,931,042 — William A. Holmes, Marblehead; Peter F. Costa, Cambridge, both of Mass. TROCAR ASSEMBLY WITH IMPROVED LATCH. Patent dated June 5, 1990. Disclaimer filed Dec. 30, 1996, by the assignee, United States Surgical Corp.

The term of this patent shall not extend beyond the expiration date of Pat. No. 4,902,280.
*(Official Gazette, April 22, 1997)*